United States Patent [19]

Ogiu et al.

[11] Patent Number: 4,791,479
[45] Date of Patent: Dec. 13, 1988

[54] COLOR-IMAGE SENSING APPARATUS

[75] Inventors: Hisao Ogiu; Toshiaki Noguchi, both of Tokyo, Japan

[73] Assignee: Olympus Optical Co., Ltd., Tokyo, Japan

[21] Appl. No.: 55,700

[22] Filed: May 29, 1987

[30] Foreign Application Priority Data

Jun. 4, 1986 [JP] Japan .............................. 61-128151
Nov. 13, 1986 [JP] Japan .............................. 61-270461

[51] Int. Cl.⁴ .......................... A61B 1/04; A61B 1/06; H04N 7/18; H04N 9/07
[52] U.S. Cl. ......................................... 358/98; 128/6; 358/42; 358/44
[58] Field of Search ................... 358/98, 42, 44; 128/6

[56] References Cited

U.S. PATENT DOCUMENTS

| | | | |
|---|---|---|---|
| Re. 31,289 | 6/1983 | Moore | 358/98 |
| 4,074,306 | 2/1978 | Kakinuma | 358/1 |
| 4,253,447 | 3/1981 | Moore | 358/98 |
| 4,491,865 | 1/1985 | Danna | 358/98 |
| 4,625,236 | 11/1986 | Fujimori | 358/98 |
| 4,646,724 | 3/1987 | Sato | 128/6 |
| 4,653,478 | 3/1987 | Nagasaki | 358/98 |
| 4,704,520 | 11/1987 | Kanno | 128/6 |

FOREIGN PATENT DOCUMENTS 3718603 5/1931 Fed. Rep. of Germany .
3410401A1 6/1987 Fed. Rep. of Germany .

Primary Examiner—Howard W. Britton
Attorney, Agent, or Firm—Ladas & Parry

[57] ABSTRACT

An electronic endoscope comprising an endoscope unit and a light source unit. The endoscope includes a light guide and a CCD for imaging the object. The light source unit includes a continuously lighting lamp (e.g., xenon lamp), for use as a light source for observation, and a flashing stroboscope as a light source for still-picture recording. An illumination light from the lamp or the stroboscope is applied alternatively to a light guide. A rotary filter is located in front of the light guide. Every time it makes one revolution, the filter colors the illumination light red, green, and blue, in succession, with shielding periods between coloring periods. The CCD is stored with signal charge corresponding to image information during a coloring period, and outputs an output signal during a shielding period thereafter. The output of the CCD is supplied to the light source unit, and is transmitted through a multiplexer to be stored in any of frame memories. The multiplexer is switched with every imaging of one color-component image by the CCD, and image signals for red, green, and blue color components are stored individually in the frame memories. Output signals for the three color components are read out simultaneously from the frame memories, and are supplied to a CRT color monitor 64 and an image filing unit. In a still-picture recording mode, the stroboscope is flashed in the following manner while the rotary filter makes one revolution. Emission of a first flashlight ends at the end of a coloring period for a first color, and a second flashlight is emitted in the middle of a coloring period for a second color. Emission of a third flashlight is started at the start of a coloring period for a third color. Thereafter, the storage into the frame memories is stopped.

13 Claims, 7 Drawing Sheets

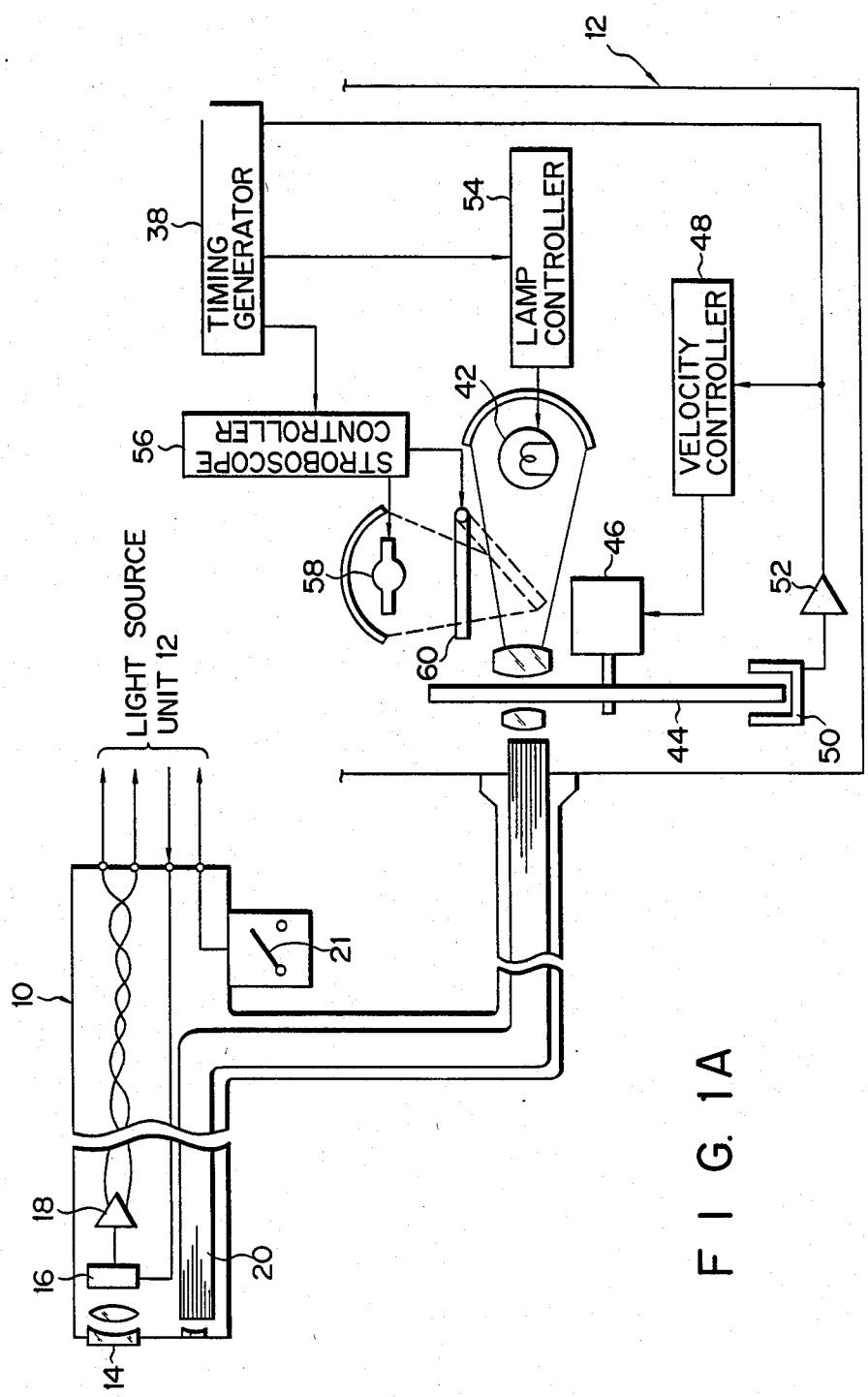
F I G. 1A

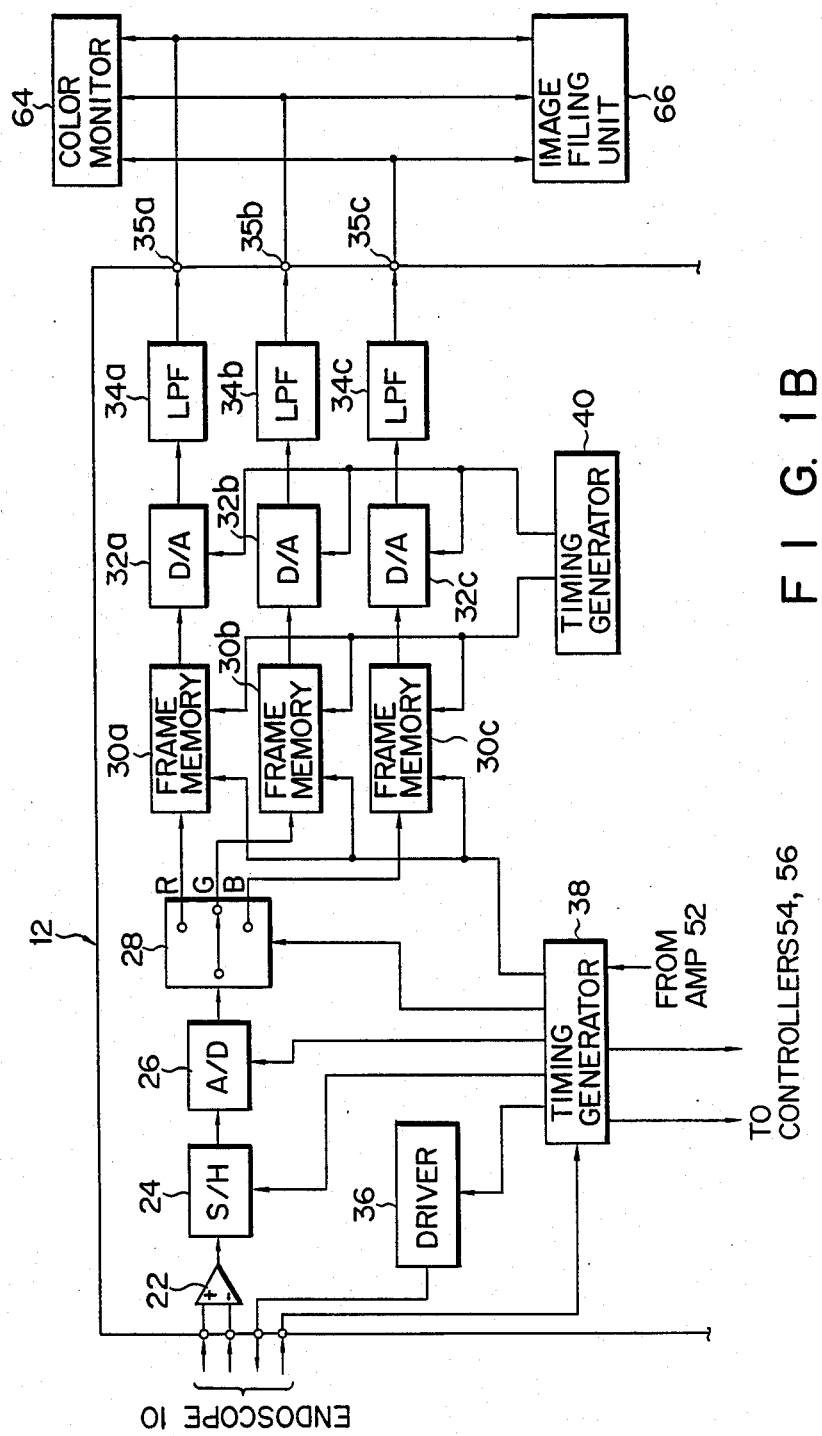
F I G. 1B

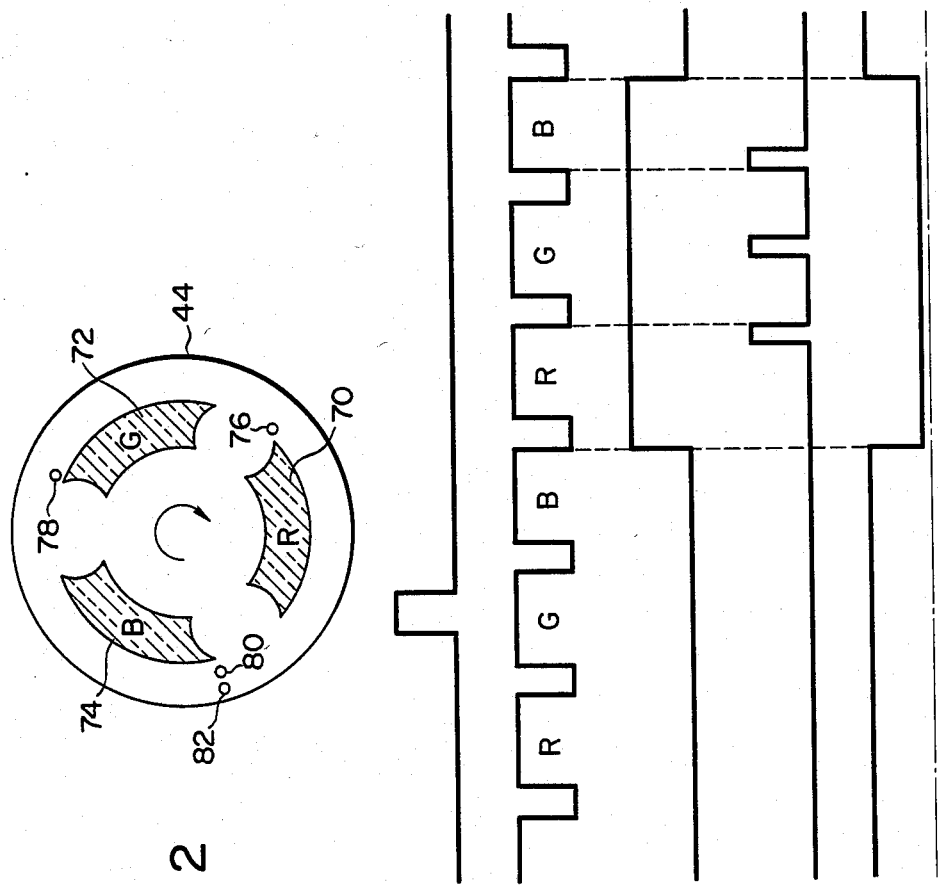

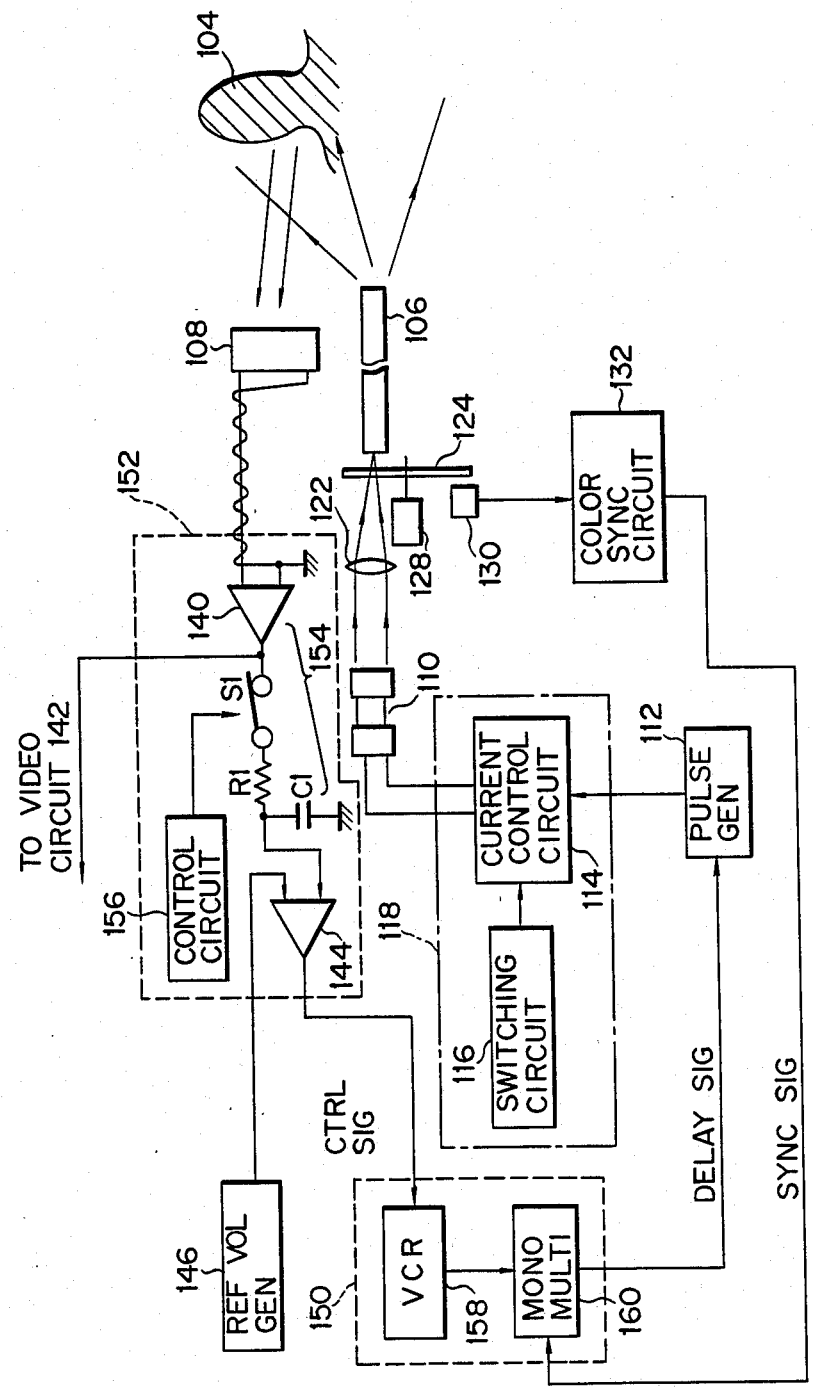
F I G. 5

COLOR-IMAGE SENSING APPARATUS

BACKGROUND OF THE INVENTION

The present invention relates to a color-image sensing apparatus which performs color-imaging according to a frame-sequential system.

As a prior art example of such a color-image sensing apparatus, there is an electronic endoscope in which a solid-state image sensing device, such as a CCD, is contained in the distal end of its insertion section. Usually, endoscopes are used for observing the inside of the body cavity or narrow tubular members, which are pitch-dark or very dark. Therefore, use of an illumination light from a light source unit is essential to the observation. Thus, in a frame-sequential electronic endoscope, a rotary filter, having red, green, and blue color components, is located in front of a lamp. As the filter makes one revolution, an illumination light, which is emitted from a light source unit and applied to a light guide of the endoscope, is colored red, green, and blue, in succession. Then, images of the individual color components are stored into their corresponding frame memories. After the images of the three color components are stored in the frame memories, they are read out simultaneously, and displayed as a resultant full-color image on a CRT monitor.

Thus, according to the frame-sequential system, three color-component images are synthesized into one full-color image. In producing a still picture of a quickly moving object, therefore, the three component images are subject to a shearing in color, and cannot provide a high-quality picture.

Such an awkward situation may possibly be avoided by increasing the rotating speed of the rotary filter to pickup the three color-component images in a shorter period of time. If this is done, however, photographing periods for the individual component images will inevitably become too short to ensure a satisfactory quantity of light for the illumination.

In a light source unit having a flashing lamp, such as a stroboscope or a lamp capable of intermittent lighting (pulse lighting), it is necessary to use a diaphragm mechanism to control exposure since the amount of flash light is constant. The diaphragm mechanism makes the light source unit complicated in structure.

These circumstances are not limited to electronic endoscopes, and hold true of any color-image sensing apparatuses of a frame-sequential system.

SUMMARY OF THE INVENTION

It is an object of the present invention to provide a color-image sensing apparatus of a frame-sequential system, capable of producing still pictures of less color shearing, without reducing the quantity of illumination light by increasing the rotating speed of a rotary filter.

Another object of the invention is to provide a color-image sensing apparatus of a frame-sequential system, capable of controlling an amount of illumination light emitted from a flashing lamp.

According to the present invention, there is provided a color-image sensing apparatus which comprises a light source for emitting a flashlight, an image sensing section for imaging an object illuminated by the light source, a filter unit having filters of at least two colors, which are to be interposed cyclically into an optical path extending from the light source to the image sensing section, a signal processing circuit for synthesizing images of at least two different color components successively output from the image sensing section to produce a full-color image, and a light-source controller for operating the light source once during the interposition of each filter of the filter unit within one cycle of interposition of the filter unit, so that emission of a first flashlight ends at the end of an interposition period for the filter of a first color component, and emission of the last flashlight starts at the start of an interposition period for the last color component.

BRIEF DESCRIPTION OF THE DRAWINGS

FIGS. 1A and 1B are block diagrams of an electronic endoscope as a color-image sensing apparatus according to a first embodiment of the present invention;

FIG. 2 is a plan view of a rotary filter used in the electronic endoscope of FIGS. 1A and 1B;

FIGS. 3A to 3E show signal waveforms for illustrating the operation of the electronic endoscope of FIGS. 1A and 1B;

FIG. 5 is a detailed block diagram showing a delay circuit and a control-signal generator according to the second embodiment;

DETAILED DESCRIPTION OF THE PREFERRED EMBODIMENTS

Figure 4:
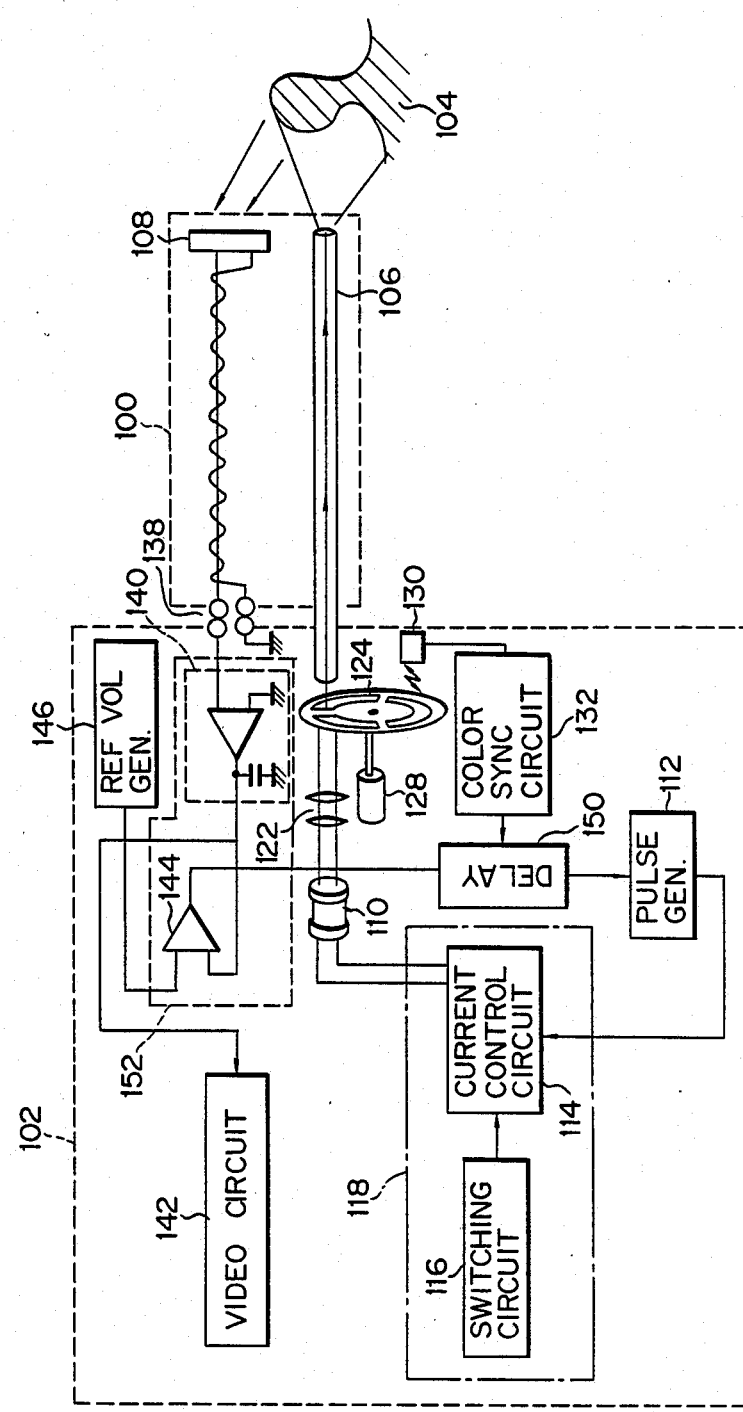
FIG. 4 is a block diagram of an electronic endoscope as a color-image sensing apparatus according to a second embodiment of the invention.

A color-image sensing apparatus according to an embodiment of the present invention will now be described in detail with reference to the accompanying drawings. In this case, an electronic endoscope will be described as an example of the sensing apparatus. FIGS. 1A and 1B are block diagrams of the endoscope. The electronic endoscope comprises endoscope unit 10 and light source unit 12. The light source unit 12 serves not only as a light source, but also both as a camera controller for controlling an image sensing device and as a video processor for processing signals from the sensing device. The endoscope unit 10 is not limited to a medical type for observing the inside of the body cavity, and may also be applied to an industrial type which is used to observe the inside of a narrow tubular member in a machine.

Objective lens 14 and solid-state image sensing device (e.g., CCD) 16, used to pickup an image of an object, are provided at the distal end of an insertion section of endoscope unit 10.

Since the distal end of endoscope unit 10 is narrow, CCD 16 is composed only of a charge-storage section (image sensing section), having no shielding section used for outputting charges. Thus, reading and storage cannot be performed simultaneously. As will be described in detail later, they are executed serially, by irradiation with an illumination light from light source unit 12 and by shielding it.

Color-component signals, which are delivered successively from CCD 16 with every frame, are supplied as two-phase signals to common-mode rejection (CMR) amplifier 22 in light source unit 12, via preamplifier 18.

Endoscope unit 10 further includes light guide 20 which is formed of a bundle of optical fibers. One end of light guide 20 is connected to light source unit 12, while the other end thereof is led to the distal end of the endoscope unit 10. The illumination light from unit 12 is transferred through guide 20 and applied to the object of observation.

The output of CMR amplifier 22 is transmitted through sample-and-hold (S/H) circuit 24, analog-to-digital (A/D) converter 26, and multiplexer 28, and is stored into any of frame memories 30a, 30b and 30c. Multiplexer 28 is switched with every imaging of a color-component frame by CCD 16. In this case, the imaging system is a frame-sequential system using three color-component frames of R, G, and B, and frame signals indicative of components R, G and B are stored into memories 30a, 30b and 30c, respectively.

The signals stored in memories 30a, 30b and 30c are simultaneously read out from the memories 30a, 30b, and 30c. The outputs of frame memories 30a, 30b and 30c are transmitted through digital-to-analog (D/A) converters 32a, 32b and 32c and low-pass filters (LPF) 34a, 34b and 34c, and are delivered from R-, G-, and B-signal output terminals 35a, 35b and 35c, respectively. CRT color monitor 64 and image filing unit 66 are connected to terminals 35a, 35b and 35c. An optical disk or the like is used for filing unit 66.

Light source unit 12 includes driver 36 for generating clock pulses used to drive CCD 16.

The individual circuits in light source unit 12 are timing-controlled by timing generators 38 and 40. For frame memories 30a, 30b and 30c, the storage speed is different from the readout speed. The storage into memories 30a, 30b and 30c is controlled by timing generator 38, so as to be synchronous with the imaging by CCD 16. The readout from memories 30a, 30b and 30c is controlled by timing generator 40, so as to be synchronous with data transfer necessary for CRT color monitor 64, image filing unit 66 and other devices connected to signal output terminals 35a, 35b and 35c. Generator 38 is connected to S/H circuit 24, A/D converter 26, multiplexer 28, frame memories 30a, 30b and 30c, and driver 36. Generator 40 is connected to memories 30a, 30b and 30c and D/A converters 32a, 32b and 32c. Timing generator 38 is supplied with a signal from release switch 21, which is provided in a handling section of endoscope unit 10.

Light source unit 12 includes different light sources for observation and for still-image recording. Lamp (e.g., xenon lamp) 42, which is adapted for continuous radiation, is used as the observation light source. Stroboscope 58 for a flashlight is used as the recording light source. Lamp controller 54 for lamp-current control is connected to lamp 42. Stroboscope 58 is connected with stroboscope controller 56 which produces a discharge current for a flashlight.

The direction of radiation of lamp 42 is at right angles to that of stroboscope 58, and movable mirror 60 is disposed near the point of intersection of the radiations. When mirror 60 is situated in the position indicated by solid line in FIG. 1A, an illumination light from stroboscope 58 is intercepted by mirror 60, and an illumination light from lamp 42 is applied to light guide 20, after passing through a relay lens and rotary filter 44. When mirror 60 is situated in the position indicated by broken line in FIG. 1, the light from lamp 42 is intercepted by mirror 60, and the light from stroboscope 58 is reflected by mirror 60 and then applied to light guide 20 through the relay lens and rotary filter 44. The displacement of mirror 60 is controlled by stroboscope control circuit 56. When lamp 42 is on, mirror 60 is situated in the solid-line position. When stroboscope 58 is on, mirror 60 is situated in the broken-line position. Lamp controller 54 and stroboscope controller 56 are controlled alternatively by timing generator 38.

As mentioned before, rotary filter 44 has a function to color the illumination light red, green, and blue, in succession, with shielding periods between coloring periods. As shown in FIG. 2, filter 44 is formed of a disk which has red, green, and blue color filter elements 70, 72 and 74 arranged circumferentially at predetermined intervals. If elements 70, 72 and 74 are situated in the optical path of the illumination light, that is, in front of light guide 20, while filter 44 is rotating, signal charge corresponding to color-component image information on the object is stored in CCD 16. When the illumination light is intercepted thereafter by those portions of the disk between filter elements 70, 72 and 74, the stored charge is read out from CCD 16. CCD 16 is switched from the storage mode to the readout mode by means of apertures 76, 78 and 80 for read-pulse generation, which are arranged outside the trailing-end portions of their corresponding filter elements 70, 72 and 74, with respect to the rotating direction thereof. Also, aperture 82 for start-pulse generation is located outside the trailing-end portion of blue filter element 74, with respect to the rotating direction.

Rotary filter 44 is driven by stepping motor 46, which is PLL-controlled by velocity controller 48. Photocoupler 50, which includes a light emitting element and a light receiving element on either side of filter 44, is located beside the peripheral edge portion of the filter. The photocoupler produces the read pulse or the start pulse when it detects aperture 76, 78, 80 or 82. The start and read pulses, delivered from photocoupler 50, are supplied to timing generator 38 and velocity controller 48 via amplifier 52.

Referring now to FIGS. 3A to 3E, the operation of the present embodiment will be described. Velocity controller 48 is provided with a reference-signal generator, which produces synchronizing pulses (e.g., at intervals of 1/30 second) as reference pulses for the control of the rotation of rotary filter 44. Thus, controller 48 makes stepping motor 46 or filter 44 at a speed synchronized with the synchronizing pulses. As filter 44 rotates in this manner, color filters 70, 72 and 74 are put successively into the optical path of the illumination light incident on light guide 22. As a result, the illumination light is colored red, green, and blue (coloring periods; high-level periods), in succession, with the shielding periods (low-level periods) between the coloring periods, as shown in FIG. 3B.

Each read pulse (not shown) is produced at the end of each illumination with red, green, or blue light, while each start pulse (not shown) is produced at the end of blue illumination. Velocity controller 48 controls the rotating speed of stepping motor 46 so that the start pulses are produced in synchronism with the synchronizing pulses.

In a normal photographing mode (when release switch 21 is not on), timing generator 38 supplies lamp controller 54 with a control signal such that lamp 42 lights, and supplies stroboscope controller 56 with a control signal such that stroboscope 58 does not flash, and that mirror 60 is situated in the solid-line position. In FIG. 3C showing the position of mirror 60, the high and low levels correspond to the positions indicated by broken and so lid lines in FIG. 1A, respectively. Thus, in the normal photographing mode, the illumination light for observation, emitted from lamp 42, is colored red, green, and blue, in succession, by means of rotary filter 44, and is then applied to light guide 20.

While the illumination light is being colored red, green, and blue, CCD 16 is stored with signal charges corresponding to image data on the individual color components. During the shielding periods directly after the coloring periods, the stored charges are read out. Thus, in response to the read pulse produced at the end of each period for illumination with red, green, or blue light, each stored charge is read out from CCD 16 and written into frame memory 30a, 30b or 30c. An image of the object, picked up in this manner, according to the frame-sequential system, is delivered from R-, G-, and B-signal output terminals 35a, 35b and 35c, and is displayed on CRT color monitor 64, on a real-time basis.

Normally, the display on color monitor 64 is a moving picture. Alternatively, however, a still picture may be displayed on the monitor for a further detailed observation of the object. The color shearing cannot be prevented by only interrupting the storage into frame memories 30a, 30b and 30c and repeatedly reading the finally stored images. According to this embodiment, therefore, still-picture recording is performed as follows.

While watching the monitor screen, an operator closes release switch 21 at a desired time for still-picture recording (FIG. 3A). In response to this, timing generator 38 is shifted from a moving-picture mode to a still-picture mode. In response to the first start pulse delivered thereafter (at the end of blue illumination thereafter), generator 38 shifts mirror 60 to the broken-line position of FIG. 1A, as shown in FIG. 3C, and causes lamp controller 54 to reduce the lamp current to a very low level, but not to zero (dashed line), as shown in FIG. 3E. Since the incidence of the illumination light from lamp 42 on light guide 20 is intercepted by mirror 60, the lamp current need not always be reduced.

In response to three read pulses, the first of which has generated simultaneously with the start pulse, and also to the two pulse generated thereafter, timing generator 38 produces timing pulses which cause stroboscope 58 to emit flashlights three times, as shown in FIG. 3D. After production of every read pulse, stroboscope controller 56 produces a timing pulse with a specific delay time. The individual delay times are determined so that emission of a first flashlight ends at the end of a red-illumination period, a second flashlight is emitted in the middle of a green-illumination period, and emission of a third flashlight starts at the start of a blue-illumination period. Each emission period of stroboscope 58 is fixed. In the still-picture mode, the illumination light is emitted only from stroboscope 58. Even during a coloring period for rotary filter 44, therefore, the quantity of illumination light is zero unless a flash is being emitted, so that imaging (storage of signal charge) cannot not be effected unless a flash is being emitted. In other words, imaging can be accomplished only while a flash is being emitted.

Thus, in the electronic endoscope according to this embodiment, the time duration between the start of imaging of the first color-component image and the end of imaging of the third color-component image is shorter than in the case of the prior art electronic endoscope in which imaging is effected during the whole coloring period. Accordingly, a still picture with less color shearing can be recorded without reducing the quantity of illumination light by increasing the rotating speed of the rotary filter. Theoretically, the flash light for green-color imaging can be emitted at any point of time during a green-coloring period. If it is emitted in the middle of the period, however, the three color-component images can be picked up at the same time interval.

When the blue-illumination period ends thereafter, timing generator 38 terminates the still-picture recording mode. In this case, mirror 60 returns to the solid-line position of FIG. 1A, as shown in FIG. 3C, and the lamp current is restored to its high level, as shown in FIG. 3E. On the other hand, the writing of signals into frame memories 30a, 30b and 30c is kept interrupted, so that the image obtained by the still-picture recording continues to be displayed on color monitor 64. When release switch 27 is depressed again after the recorded still-image is stored in image filing unit 66, the signals restart to be written into memories 30a, 30b and 30c, and color monitor 64 returns to the moving-picture display mode.

Although both lamp 42 and stroboscope 58 are used for the light source in the embodiment described above, stroboscope 58 alone may serve fully for the purpose. In this case, if the red, green, and blue filter elements are different in circumferential length (corresponding to coloring time), the quantity of light emitted from the stroboscope must be changed by controlling the emission frequency and emission time of the stroboscope correspondingly. The sensitivity of the CCD to the individual colors is lowered in the order of red, green, and blue, so that the order of size of the filter elements is blue, green, and red. In this case, therefore, smallest element R should only be situated in the position for element G of this embodiment, that is, color component R should be the second component.

Exposure control of an electronic endoscope, having only the flashing lamp, will now be described. In this specification, the flashing lamp includes a stroboscope and a lamp capable of intermittent lighting (pulse lighting). FIG. 4 is a block diagram of such an endoscope according to a second embodiment of the present invention.

Light source unit 102 is connected to electronic endoscope 100. Endoscope 100 comprises light guide 106 and charge-coupled device (CCD) 108. Light guide 106 is composed of a bundle of optical fibers which guides an illumination light, emitted from light source unit 102, to the distal end of an insertion section, thereby lighting object 104. CCD 108 is a solid-state image sensing device which is contained in the distal end of the insertion section.

Light source unit 102 includes a lamp capable of intermittent lighting (e.g., xenon lamp) 110 as a light source. When the output pulse signal of pulse generator 112 is applied to current control circuit 114, lamp 110, which is subject to constant-current control, emits a flashlight in synchronism with the pulse signal. Switching circuit 116 is connected to current control circuit 114. Circuits 114 and 116 constitute lighting circuit 118.

The light emitted from lamp 110 is transmitted through optical lens system 122 and rotary filter 124, and is then applied to light guide 106 of electronic endoscope 100. Filter 124, which is rotated by motor 128, is used to color the illumination light red (R), green (G), and blue (B), in succession. Shielding periods are interposed between coloring periods for the individual color components. Optical sensor 130 is used to detect the coloring periods for the color components of filter 124. When each coloring period terminates, sensor 130 delivers a pulse to color synchronizing circuit 132. Circuit 132 supplies a color synchronizing signal to delay circuit 150 for a fixed period of time (equivalent to the coloring period) after a predetermined period (equivalent to the shielding period) subsequent to the reception of the synchronizing pulse.

An output signal from CCD 108 is supplied to light source unit 102 through signal lines and connector 138 in electronic endoscope 100. This signal is applied to the input of signal processing circuit 140, which performs amplification, clamping, and various correcting operations. The output of circuit 140 is supplied to video circuit 142, and an image appears on a display section (not shown). The same output is also applied to differential amplifier 144, which is supplied with a reference signal by reference-voltage generator 146. Signal processing circuit 140 and amplifier 144 form a control-signal generator 152. The output of amplifier 144 is fed to delay circuit 150, which delays the output of color synchronizing circuit 132 in accordance with the output of amplifier 144.

FIG. 5 shows the details of delay circuit 150 and control-signal generator 152 according to the second embodiment. The output of CCD 108 is applied to signal processing circuit 140. The output of circuit 140 is supplied to integrator 154 which is composed of switch S1, resistor R1, and capacitor C1. The operation of switch S1 is controlled by means of control circuit 156. The output of integrator 154 is supplied to differential amplifier 144.

Delay circuit 150 includes voltage-controlled resistor (VCR) 158 and monostable multivibrator 160. The resistance value of VCR 158 changes according to applied voltage. The output of differential amplifier 144 is applied to VCR 158. VCR 158 serves to determine the time constant of multivibrator 160. The output of color synchronizing circuit 132 is supplied to multivibrator 160 whose output is supplied to pulse generator 112.

Figure 6:
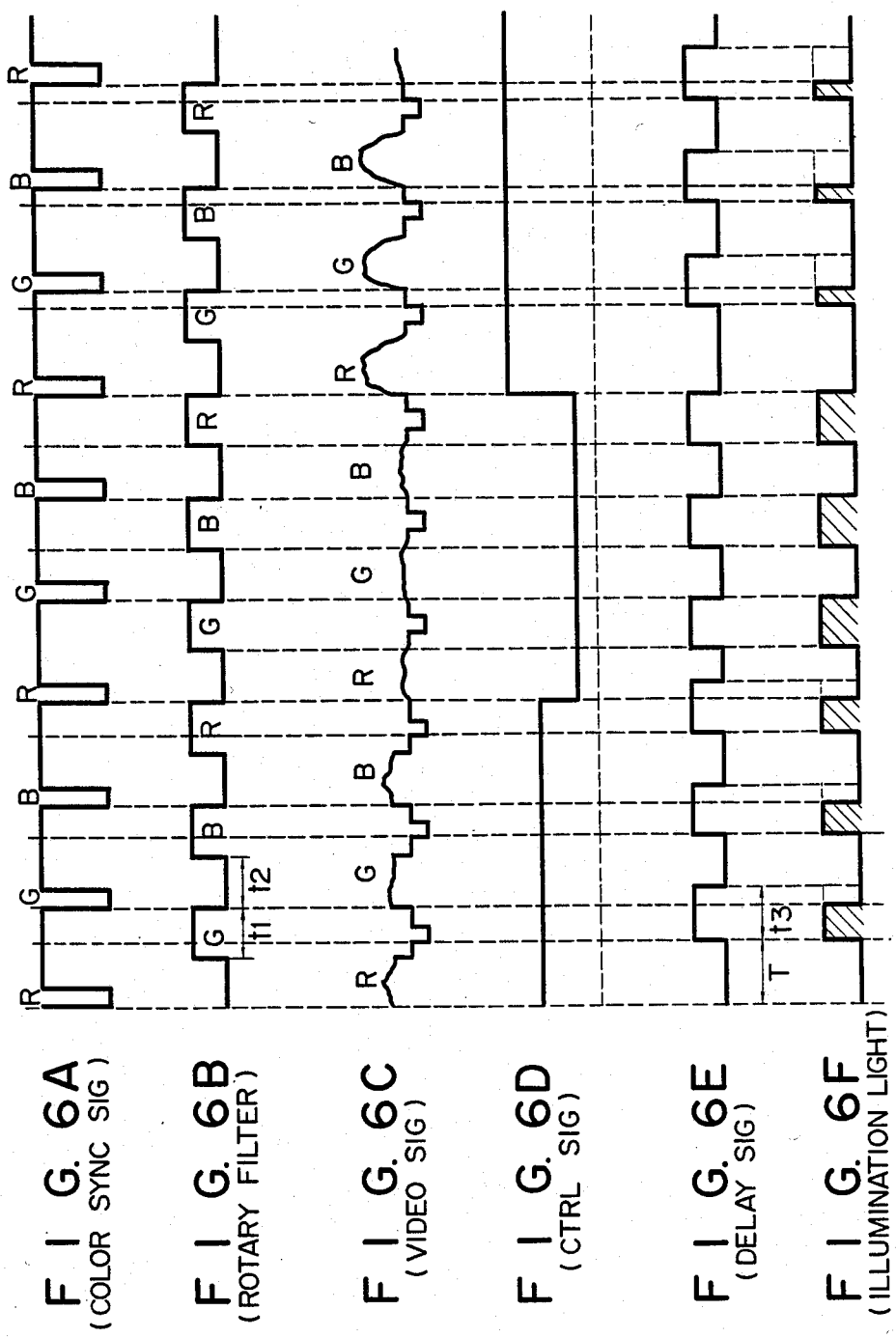
FIGS. 6A to 6F show signal waveforms for illustrating the operation of the apparatus of the second embodiment.

Referring now to the timing charts of FIGS. 6A to 6F, the operation of the electronic endoscope of FIG. 4 will be described. As rotary filter 124 rotates, color synchronizing signals (negative pulses) are delivered from color synchronizing circuit 132, as shown in FIG. 6A. FIG. 6B illustrates the manner of filtering by filter 124. In FIG. 6B, t1 and t2 designate the coloring period and shielding period, respectively. At the end of each coloring period, a color synchronizing signal is delivered, and triggers monostable multivibrator 160. In this embodiment, the time constant of multivibrator 160 is determined by VCR 158 whose resistance value varies, depending on the output of control-signal generator 152. The output level of multivibrator 160 rises when a time equivalent to the time constant passes after the vibrator 160 is triggered. Then, multivibrator 160 delivers output pulses of a fixed width. The resistance value of VCR 158 increases and decreases as the level of the control signal increases and decreases, respectively. Accordingly, the delay time of delay circuit 150 also changes corresponding to the level of the control signal.

FIG. 6C shows the way the video signal from CCD 108 behaves when the brightness of the object varies from medium to low and from low to high. The video signal is integrated by integrator 154, and the result of the integration for each frame is held in capacitor C1. FIG. 6D shows the integration output, which is supplied to one input terminal of differential amplifier 144. In FIG. 6D, a broken line indicates the reference signal which is supplied to the other input terminal of amplifier 144. The difference between the reference signal and the integration signal is applied as a control signal or voltage to VCR 158. Thus, the higher the brightness of the object, the longer the delay time of delay circuit 150 will be.

A delay signal, which is delayed by time T, corresponding to the brightness of the object, after the delivery of the color synchronizing signal (FIG. 6A), is supplied from monostable multivibrator 160 to pulse generator 112. FIG. 6E shows the delay signal. During period t3 when the delay signal is generated, generator 112 causes lighting circuit 118 to flash lamp 110. When the brightness of the object is medium or high, shielding period t2 of the rotary filter starts before flashing period t3 ends. When the brightness of the object is low, shielding period t2 starts at the end of flashing period t3. Therefore, the illumination light is intercepted during the latter half of the flashing period when the brightness is medium or high, as shown in FIG. 6F. Thus, the light from lamp 110, incident on light guide 106, is smaller in quantity than in the case where the brightness of the object is low. In consequence, automatic exposure control can be effected without using any diaphragm.

Flashing period t3, coloring period t1, shielding period t2, and delay time T must have the following correlations.

$$t3 < t2, \quad (1)$$

$$t1 + t2 > T + t3. \quad (2)$$

According to this embodiment, as described above, there is provided a light source unit for an endoscope, in which the timing for the start of the flashing of the lamp is delayed behind the start of the coloring of the rotary filter, in accordance with a light-control signal, so that automatic exposure control can be effected with use of a simple construction including no diaphragm means.

Since the control signal is determined on the basis of the difference between the integration output and the reference signal, the exposure can be adjusted to a desired brightness by changing the reference voltage.

Figure 7:
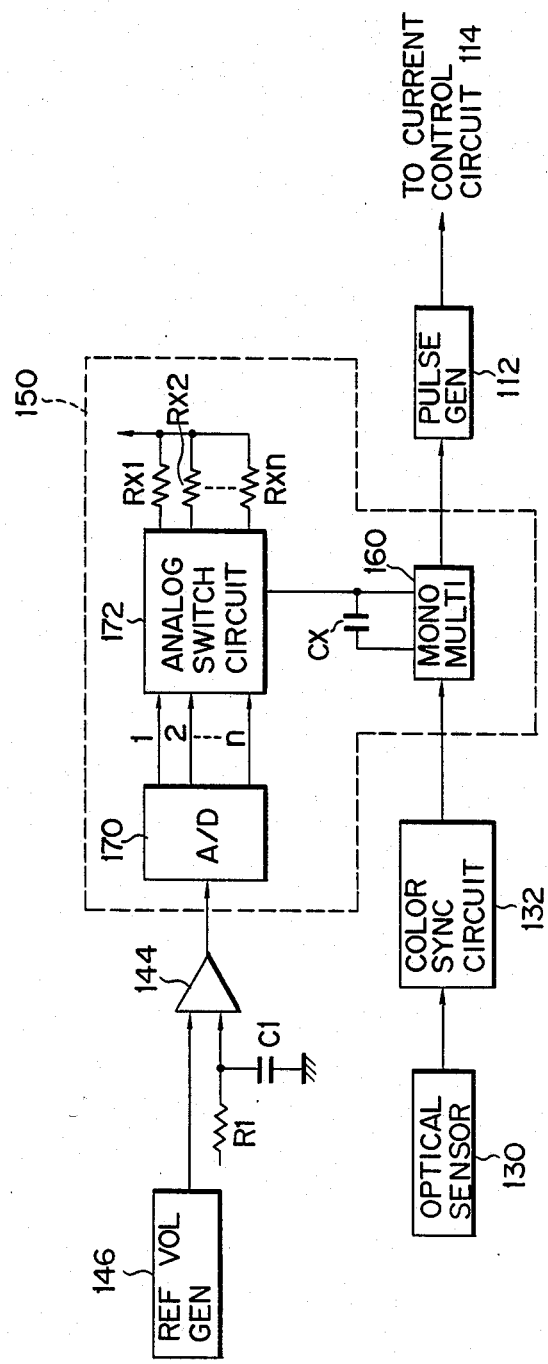
FIG. 7 is a block diagram of an electronic endoscope as a color-image sensing apparatus according to a third embodiment of the invention.

The block diagram of FIG. 7 is different from FIG. 5 only in the configuration of delay circuit 150. The output of differential amplifier 144 is applied to A/D converter 170. Only one of outputs 1 to n of converter 170 is activated so that only its corresponding analog switch in analog switch circuit 172 is turned on. As a result, any one of external resistors Rx1 to Rxn is selected and connected to the time-constant circuit of monostable multivibrator 160, so that the time constant is determined by Rxi (i=1~n) and Cx. Also in the arrangment of FIG. 7, therefore, a delay signal, which is delayed from the color synchronizing signal in accordance with the light-control signal, is supplied to pulse generator 112. Thus, the start of the flashlight emission of lamp 110 is delayed, thereby effecting automatic exposure control.

Lamp 110 may be a DC arc-discharge lamp, stroboscopic lamp, or any other conventional lamps which can emit a flashlight or can intermittently light to irradiate a pulsed light. The flashlight emission, as mentioned herein, should permit increase and decrease of the light quantity, depending on the variation of the lamp current. Therefore, the lamp need not always be turned off during the shielding period. Moreover, delay circuit 150 may be designed so that its delay time can be adjusted manually instead of using the light-control signal. In other words, the automatic exposure control may be replaced with manual exposure control.

According to the embodiment described above, there may be provided an electronic endoscope which has exposure control means of a simple construction, requiring neither mechanical diaphragm means nor diaphragm drive mechanism. Thus, the apparatus requires only a smaller number of components, and can therefore enjoy improved compactness and reduction in cost.

It is to be understood that the present invention is not limited to the embodiments described above, and that various changes and modifications may be effected therein by one skilled in the art without departing from the scope or spirit of the invention. The color components of the rotary filter are not limited to red, green, and blue, and may alternatively include yellow, magenta, and cyan. Alternatively, moreover, rotary filter may have only two color components, not three. According to the embodiment described above, furthermore, the individual color filter elements of the rotary filter are equal in size or circumferential length. However, the sensitivity of the CCD varies according to color. Actually, therefore, the filter elements must be varied in size, in order that the individual color-component images are exposed equally.

In the above embodiments, moreover, the image sensing device is contained in the distal end of the endoscope. Alternatively, a TV camera may be mounted externally on the eyepiece portion of a conventional fiberscope. Further, the present invention is not limited to the electronic endoscopes, and may also be applied to conventional color-image sensing apparatuses of a frame-sequential system. More specifically, instead of coloring the illumination light, the filter may be located in front of the CCD so that the image information is decomposed for each color component during the imaging process. Also in this case, the emission timing for the light source lamp is controlled in the same manner as aforesaid.

According to the present invention, as described above, the lamp is flashed for imaging during only part of the coloring period for each color. The imaging operation for the first color component is performed immediately before the end of the coloring period, while the imaging operation for the last color component is performed immediately after the start of the coloring period. In this manner, the imaging operation for all colors can be accomplished intensively within a relatively short period of time. Thus, still pictures with less color shearing can be recorded without reducing the quantity of illumination light by increasing the rotating speed of the rotary filter.

What is claimed is:

1. A color-image sensing apparatus comprising:
   light source means for emitting a flashlight;
   image sensing means for imaging an object illuminated by said light source means;
   filter means having at least two filters of respectively different colors for interposition cyclically into an optical path extending from said light source means to said image sensing means;
   light source control means for detecting when each filter of said filter means is interposed in said optical path and causing said light source means to emit said flashlight after a lapse of time after said detection, said time being variable; and
   signal processing means for synthesizing images of at least two different color components delivered successively from said image sensing means, thereby producing a full-color image.

2. The color-image sensing apparatus according to claim 1, in which said filter means includes filters of at least two different colors, which are to be interposed cyclically into an optical path extending from said light source means to said image sensing means and between which a shielding member is interposed, and said light source control means includes means for detecting the brightness of the object and means for operating said light source means after delay from the start of an interposition period for each filter in said optical path in accordance with the brightness detected by said detecting means.

3. The color-image sensing apparatus according to claim 1, in which said light source control means operates said light source control means once during an interposition period of each filter of said filter means within one cycle of interposition of said filter means, so that emission of a first flashlight ends at the end of an interposition period for the filter of a first color component and emission of the last flashlight starts at the start of an interposition period for the filter of a last color component.

4. The color-image sensing apparatus according to claim 3, in which said filter means includes filters of three different color components, and said light-source control means controls the light source so that a second flashlight is emitted in the middle of an interposition period for a second color component.

5. An electronic endoscope comprising:
   an endoscope unit including light guide means;
   light source means connected to said endoscope unit for supplying an illumination light to an object through said light guide means;
   filter means located between said light source means and said light guide means, and having at least two filters of respectively different colors for interposition cyclically into an optical path of said illumination light;
   image sensing means provided at a distal end of the endoscope unit;
   memory means connected to said endoscope unit for storing image signals of individual color components delivered successively from said image sensing means and simultaneously outputting all stored image signals for the color components; and
   still-picture recording means for flashing said light source means once during each said interposition of each filter of said filter means at respectively different times relative thereto such that, within one cycle of said interposition of each filter of said filter means, a first said flashing ends at the end of said interposition of a first of said filters and another said flashing starts at the start of said interposition another of said filters, said recording means interrupting the storage of the signals into said memory means when the one cycle of interposition ends.

6. The electronic endoscope according to claim 5, in which said light source means includes a lamp lighting continuously, a stroboscope emitting a flashlight, and opticalpath switching means adapted to cause a light from the lamp to be incident on the light guide means in an observation mode, and to cause the flashlight from the stroboscope to be incident on the light guide means in a still-picture recording mode.

7. The electronic endoscope according to claim 5, in which said filter means includes filter elements of three different color components, and said still-picture recording means emits a second flashlight in the middle of a period during which the filter member of a second color is in the optical path.

8. The electronic endoscope according to claim 5, in which said filter means includes a disk-shaped rotary filter having filter elements of at least two different colors, arranged along the circumferential direction thereof.

9. The electronic endoscope according to claim 8, in which the other portions of said rotary filter than the filter elements are formed of a shielding member, and said image sensing means is switched between a storage mode and a readout mode, depending on the rotation of the rotary filter, so that the storage mode is established while any of the filter elements is in the optical path, and that the readout mode is established while the shielding member is in the optical path.

10. An electronic endoscope comprising:
an endoscope unit including light guide means;
light source means connected to said endoscope unit and for supplying a flashlight to an object of imaging through said light guide means;
filter means located between said light source means and said light guide means, and having at least two filters of respectively different colors which are to be interposed cyclically into an optical path and between which a shielding member is interposed;
image sensing means provided at a distal end of the endoscope unit;
image synthesizing means connected to said endoscope unit and for storing image signals for individual color components delivered successively from said image sensing means and simultaneously outputting all stored image signals for the color components;
means for detecting the brightness of the object; and
light source control means synchronized with the operation of said filter means for causing said light source means to emit said flashlight after delay from the start of an interposition period for each filter in said optical path in accordance with the brightness detected by said detecting means.

11. The electronic endoscope according to claim 10, in which said filter means includes a disk-shaped rotary filter of a shielding type provided with filters of at least two different colors arranged along the circumferential direction thereof, and said image sensing means is switched between a storing mode and a readout mode depending on the rotation of the rotary filter, so that the storage mode is established while any of the filters is in the optical path, and that the readout mode is established while the shielding member is in the optical path.

12. The electronic endoscope according to claim 10, in which said light source control means comprises delay means including a monostable multivibrator whose time constant is variable and means for integrating the output of said image sensing means and for varying the time constant of said monostable multivibrator in accordance with the integrated value.

13. The electronic endoscope according to claim 12, in which said filter means includes means for producing synchronizing pulses at the start of an interposition period for each filter in said optical path and supplying the synchronizing pulses to said monostable multivibrator.

* * * * *